(12) United States Patent
Long (10) Patent No.: US 7,344,534 B2
(45) Date of Patent: Mar. 18, 2008

(54) ABLATION DEVICE (75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 516 days.

(21) Appl. No.: 10/934,674

(22) Filed: Sep. 3, 2004

(65) Prior Publication Data
US 2006/0052769 A1   Mar. 9, 2006

(51) Int. Cl.
A61B 18/18    (2006.01)
(52) U.S. Cl. .......................................... 606/41; 606/46
(58) Field of Classification Search .................. 606/41, 606/45–50; 607/101, 102
See application file for complete search history.

(56) References Cited

U.S. PATENT DOCUMENTS

| 5,395,327 | A |   | 3/1995  | Lundquist et al. |        |
|-----------|---|---|---------|------------------|--------|
| 5,536,267 | A | * | 7/1996  | Edwards et al.   | 606/41 |
| 6,004,332 | A | * | 12/1999 | Yoon et al.      | 606/144|
| 6,022,334 | A |   | 2/2000  | Lundquist et al. |        |
| 6,086,583 | A |   | 7/2000  | Ouchi            |        |
| 6,254,598 | B1| * | 7/2001  | Edwards et al.   | 606/41 |
| 6,394,949 | B1|   | 5/2002  | Crowley et al.   |        |
| 6,645,201 | B1| * | 11/2003 | Utley et al.     | 606/41 |
| 2002/0183739 | A1| * | 12/2002 | Long          | 606/41 |

FOREIGN PATENT DOCUMENTS

WO    WO 01/05318 A1    1/2001
WO    WO 01/24721 A1    4/2001

OTHER PUBLICATIONS

EPO Search Report dated Apr. 22, 2005 for corresponding patent application, European Patent Application No. EP 03 255 823.1.

* cited by examiner

Primary Examiner—Michael Peffley
(74) Attorney, Agent, or Firm—Welsh & Flaxman LLC (57) ABSTRACT A medical device for performing a therapeutic procedure on a patient. The medical device comprises a probe having an applicator end and at least two injection needles connected to the probe adjacent the applicator end of the probe. Each injection needle is communicative with a fluid source for delivering fluid to the respective needle and an energy source for delivering energy to the respective needle when performing the therapeutic procedure on the patient. The medical device also includes a spreader positioned adjacent the applicator end between the injection needles for spreading tissue of the patient during the therapeutic procedure.

15 Claims, 12 Drawing Sheets

ABLATION DEVICE

FIELD OF INVENTION

The present invention relates to a medical device, and more particularly to an ablation device for ablating tissue from a patient.

BACKGROUND OF THE INVENTION

Various devices and methods have been traditionally used to combat a physical condition known as Barrett's esophagus. Barrett's esophagus is the abnormal growth of intestinal type cells into the esophagus resulting from stomach acid chronically refluxing into the esophagus. Most people occasionally experience heartburn, which is the refluxing of stomach acid beyond the lower esophageal sphincter muscle and into the esophagus. Such occasional heartburn is not harmful. Severe or frequent reflux, however, is harmful and known by the names gastroesophageal reflux disease (GERD) and chronic reflux esophagitis (also known as Chronic Acid Reflux, or CAR). About one out of every ten patients with GERD/CAR are found to have Barrett's esophagus. In patients with Barrett's esophagus, the healthy mucosal cells of the inner layer or the squamous epithelium of the esophagus are replaced with diseased or intestinal cells. It is believed that such growth is a defense mechanism of the body to avoid esophageal injury due to the acid refluxed from the stomach. Unfortunately, these mucosal tissue changes may lead to low, then high grade dysplasia, and eventually to cancer of the lower esophagus, known as adenocarcinoma.

A common method for destroying diseased esophageal tissue has been to cauterize or coagulate the unwanted tissue with a conventional ablation device. Ablation devices have developed as an alternative to other traditional means for eliminating unwanted tissue, such as cutting away the tissue, cryotherapy, and thermal therapy. Cryotherapy is the application of extreme cold to freeze and destroy diseased mucosal tissue. Thermal therapy is the application of heat to coagulate, cauterize and/or ablate diseased mucosal tissue. Sufficient raising or lowering of tissue temperature causes necrosis of the tissue. For convenience, the term ablate will be used herein to describe any and all of these thermal therapy processes. In use, these devices are placed adjacent the unwanted tissue and tissue is ablated, cauterized, coagulated, frozen, or burnt, as the case may be, by energy transmitted from or to the device.

Traditional ablation devices have two primary shortcomings. First, traditional devices can ablate only relatively small portions of patient tissue at one time. For example, ablation devices having a surface for ablating patient tissue by transmitting energy to or from the device can only ablate an area of patient tissue substantially equal to the area of the transmission surface in a single energy transmission. Further, traditional ablation devices can only ablate one side of an esophagus at any one time.

A second primary shortcoming of traditional ablation devices is their inaccuracy in use. A primary challenge for battling Barrett's esophagus is to destroy targeted tissue without affecting healthy adjacent esophageal cells or muscular cells underlying the diseased and healthy tissue. Injury to the healthy underlying muscular tissue, for example, can lead to the creation of a stricture or constriction in the esophagus. Many traditional ablation devices ablate targeted tissue without first isolating the targeted tissue from the adjacent and underlying healthy tissue. As a result, when too much energy is transferred to or from the device, ablation of healthy adjacent cells and/or underlying muscular cells can occur. On the other hand, when too little energy is transferred from the device, less than all of the targeted tissue is ablated.

The conventional approaches for treating Barrett's esophagus or other diseases requiring the precise ablation of relatively large areas of intralumenal tissue are insufficient in these regards. Thus, there is a need for an ablation device and method for using such a device that allow accurate and minimally invasive ablation of relatively large amounts of intralumenal patient tissue.

BRIEF SUMMARY OF THE INVENTION

The present invention includes a medical device for performing a therapeutic procedure on a patient. The medical device comprises a probe having an applicator end and at least two injection needles connected to the probe adjacent the applicator end of the probe. Each of the injection needles is communicative with a fluid source for delivering fluid to the respective needle and an energy source for delivering energy to the respective needle when performing the therapeutic procedure on the patient. The medical device also includes a spreader positioned adjacent the applicator end between the injection needles for spreading tissue of the patient during the therapeutic procedure.

In another aspect, the present invention includes a medical device for performing a therapeutic procedure on a patient. The medical device comprises an elongate endoscope extending to a working end and having optics for viewing an object positioned in a viewing area adjacent the working end of the endoscope. The device also includes a probe having an applicator end positioned adjacent the working end of the endoscope. The device further includes at least two injection needles positioned adjacent the applicator end of the probe in the viewing area. Each of the injection needles is communicative with a fluid source for delivering fluid to the respective needle and an energy source for delivering energy to the respective needle when performing the therapeutic procedure on the patient. Yet further, the device includes a spreader positioned adjacent the applicator end of the probe between the injection needles for spreading tissue of the patient during the therapeutic procedure.

In yet another aspect, the present invention includes a method for performing therapy on a patient. The method comprises guiding a working end of an endoscope to a desired intracavital location within the patient. The method also includes deploying a spreader adjacent the working end of the endoscope and deploying at least two injection needles to a position adjacent the working end of the endoscope, wherein each of the needles are on opposite sides of the spreader. The method further includes expanding the spreader so the spreader presses into opposite sides of the cavity thereby forcing the opposite sides of the cavity away from each other and points on the cavity intermediate the opposite sides toward each other. Yet further, the method includes injecting fluid through the needles into the points on the cavity forced toward each other and ablating inner portions of the cavity intermediate the opposite sides of the cavity by applying energy to the inner portions through the needles.

Other aspects of the present invention will be in part apparent and in part pointed out hereinafter.

BRIEF DESCRIPTION OF THE FIGURES

Corresponding reference characters indicate corresponding parts throughout the several views of the drawings.

DETAILED DESCRIPTION OF THE INVENTION

The present invention relates to a medical device for performing a therapeutic procedure on a patient, and more particularly for ablating unwanted tissue within a patient. Referring now to the figures, and more particularly to FIG. 1, a medical device according to a first embodiment of the present invention is designated in its entirety by reference number 10. The medical device has an elongate probe 12 extending to an applicator end 14. Applicator elements 16 are connected to the probe 12 adjacent the applicator end 14 of the probe 12. Although the probe 12 may be made of other materials without departing from the scope of the present invention, in one embodiment the probe is made of a flexible and thermally and/or electrically insulating material, such as silicone, polyethylene, or polypropylene. Although the probe 12 may have other shapes without departing from the scope of the invention, in one embodiment the probe is generally tubular. Further, although the probe 12 may have other dimensions without departing from the scope of the present invention, in one embodiment the probe has a maximum width 17 of between about 1 millimeter and about 5 millimeters. Having a maximum width 17 less than about three millimeters allows the probe 12 to fit inside the working channel of a standard endoscope (not shown in FIGS. 1-6). The probe may have one or more traction elements 18. The traction element 18 may be a handle.

Figure 2:
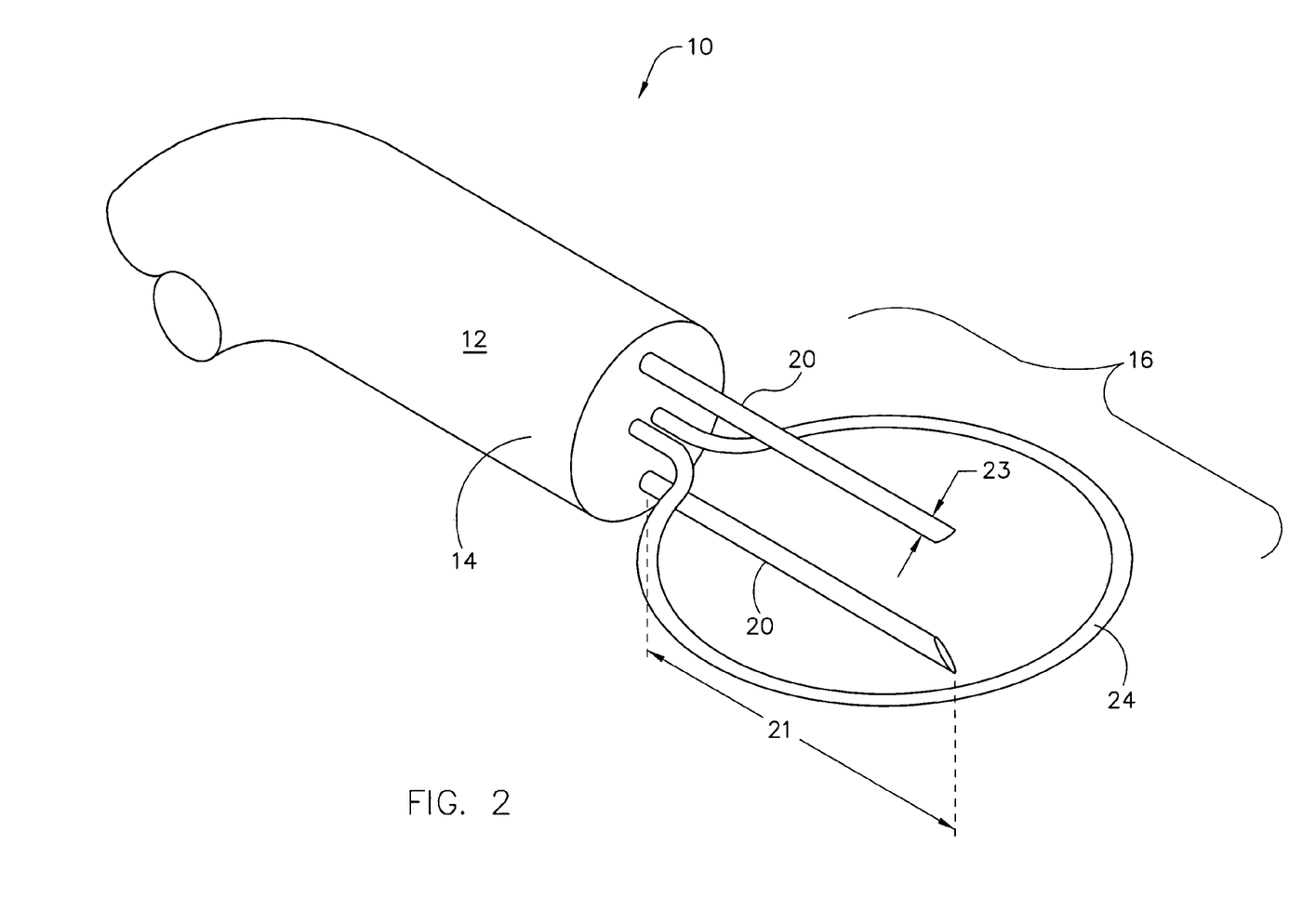
FIG. 2 is a detail perspective of the embodiment of a medical device shown in FIG. 1.

As shown in FIG. 2, the applicator elements 16 include at least two injection needles 20 connected to the probe 12 near the applicator end 14 of the probe. Although the needles 20 may have other dimensions without departing from the scope of the present invention, in one embodiment the needles 20 each have a maximum length 21 of between about 10 millimeters and about 20 millimeters and an outer diameter 23 of between about 0.5 millimeters and about 2 millimeters. Also, although the needles 20 may be made of other materials without departing from the scope of the present invention, in one embodiment the needles are made of any material traditionally used to make medical needles, such as 23 gage stainless steel. Further, although the needles 20 are shown as being substantially straight, the needles may have other shapes without departing from the scope of the invention. For example, in one alternate embodiment the needles 20 may be curved (not shown). Although the needles may be spaced by other distances without departing from the scope of the present invention, in one embodiment the needles 20 are spaced by a distance of between about 5 millimeters and about 15 millimeters.

Figure 3:
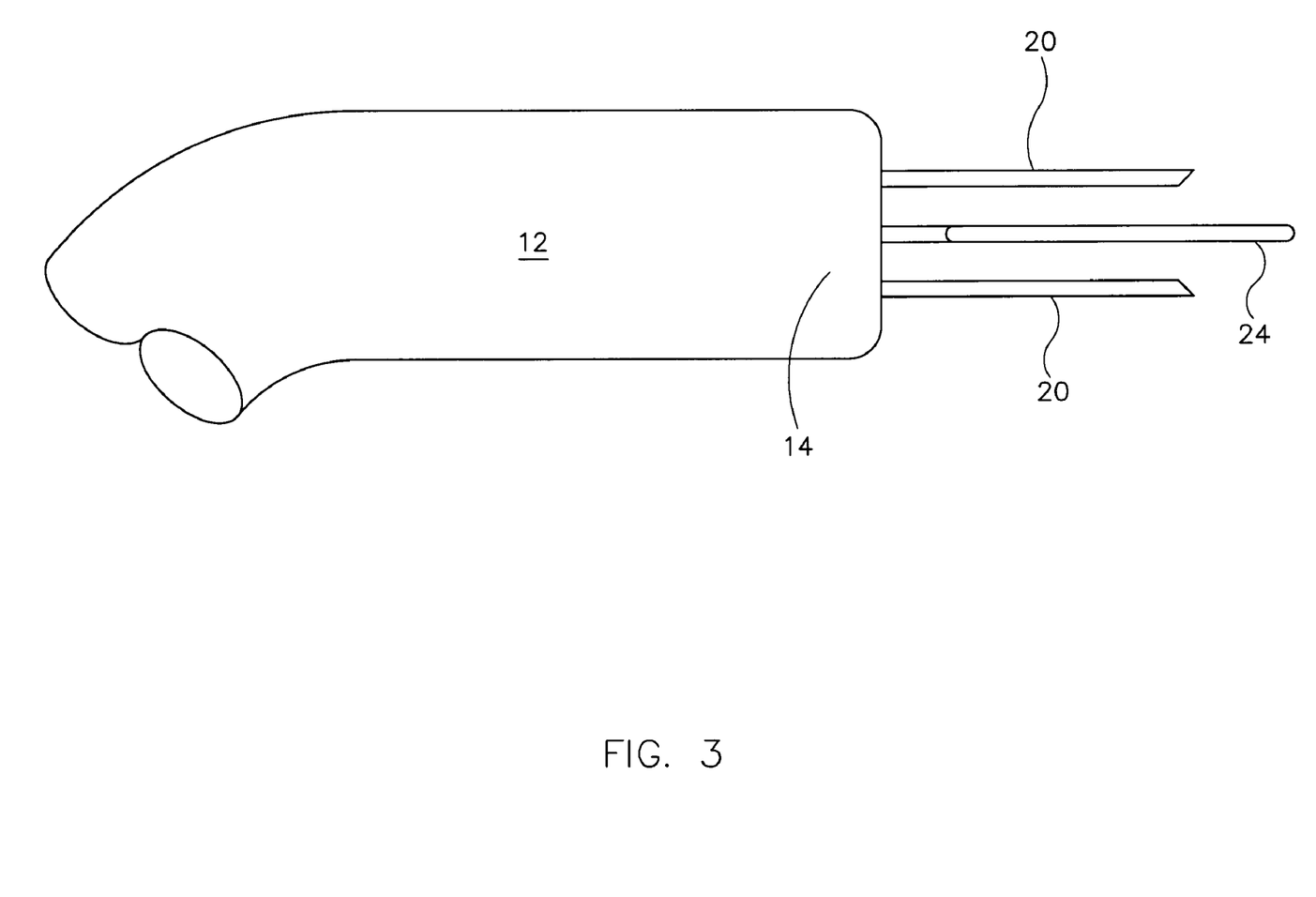
FIG. 3 is a detail side view of the medical device.
Figure 4:
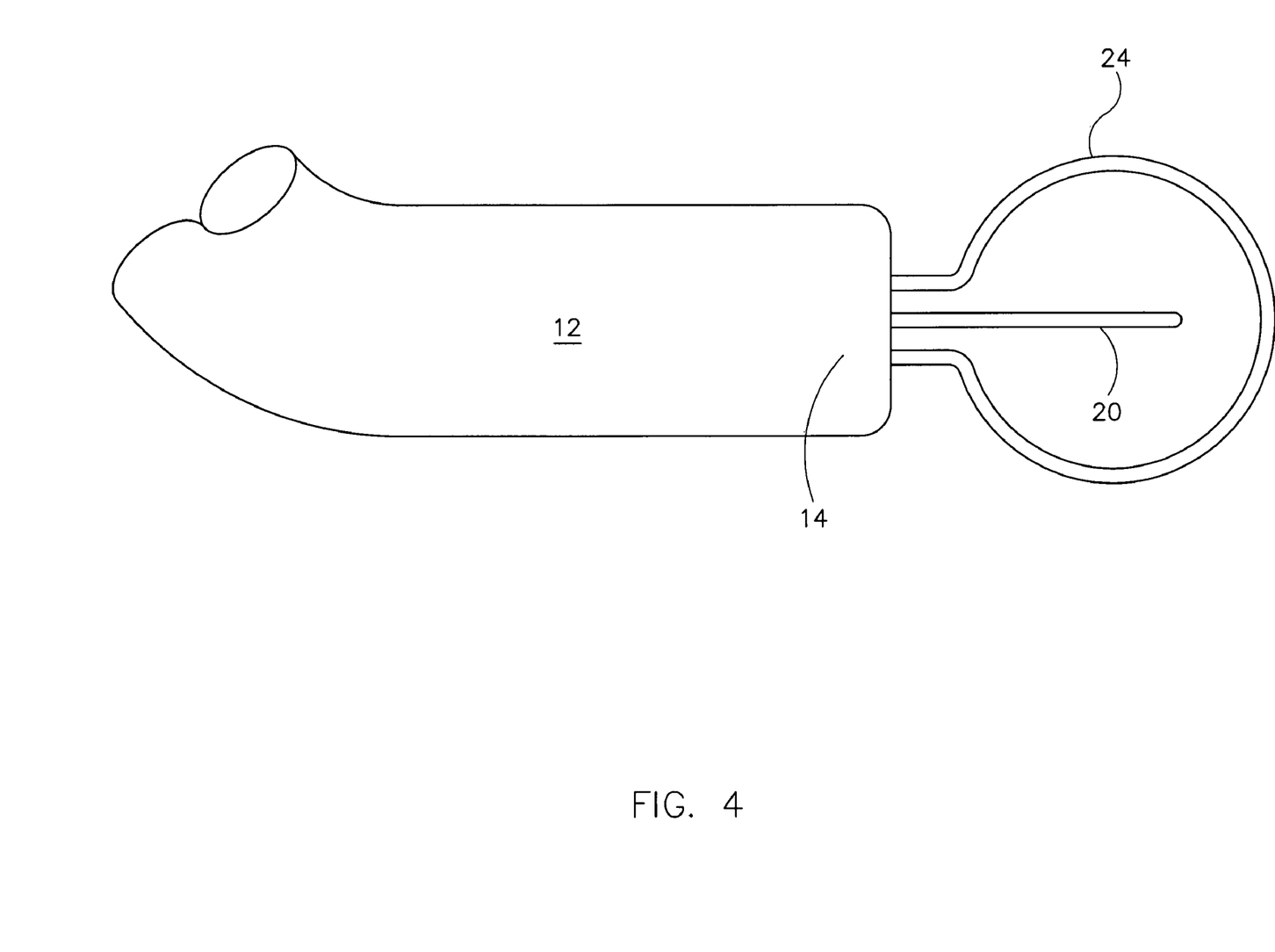
FIG. 4 is a detail top view of the medical device.

The applicator elements 16 also include a spreader 24 positioned near the applicator end 14 of the probe 12 for spreading tissue of the patient (not shown in FIGS. 1-9) during the therapeutic procedure. The spreader 24 is positioned between the injection needles 20, as shown in FIG. 3, and oriented so the spreader extends transverse to an imaginary plain (not shown) extending between the needles. Although the spreader may have other shapes without departing from the scope of the present invention, in one embodiment the spreader 24 is a generally circular loop. As shown in the top (or bottom) view of the device 10 in FIG. 4, the spreader 24 and needles 20 are substantially centered about the horizontal center of the probe 12. Although the spreader 24 may be made of other materials without departing from the scope of the present invention, in one embodiment the spreader is made of a resilient material with shape memory, such as nitonol. When the spreader 24 is made of a material having shape memory, the spreader can be formed with a shape bias. That is, the spreader 24 can be formed with a bias towards a deployed shape (shown in FIGS. 1-5, 7-9, 11, and 12) or extended position in which laterally opposite sides of the spreader are spaced from each other by a distance. Thus, the spreader returns to the deployed shape after being released from a stored shape (shown in FIGS. 6 and 10) or retracted position in which the shape of the spreader is restricted and the laterally opposite sides are closely spaced adjacent each other or touching. Although the laterally opposite sides of the spreader may be spaced by other distances when the spreader is in the extended position without departing from the scope of the present invention, in one embodiment the laterally opposite sides of the spreader 24 are spaced by a distance of between about 20 millimeters and about 50 millimeters.

Figure 1:
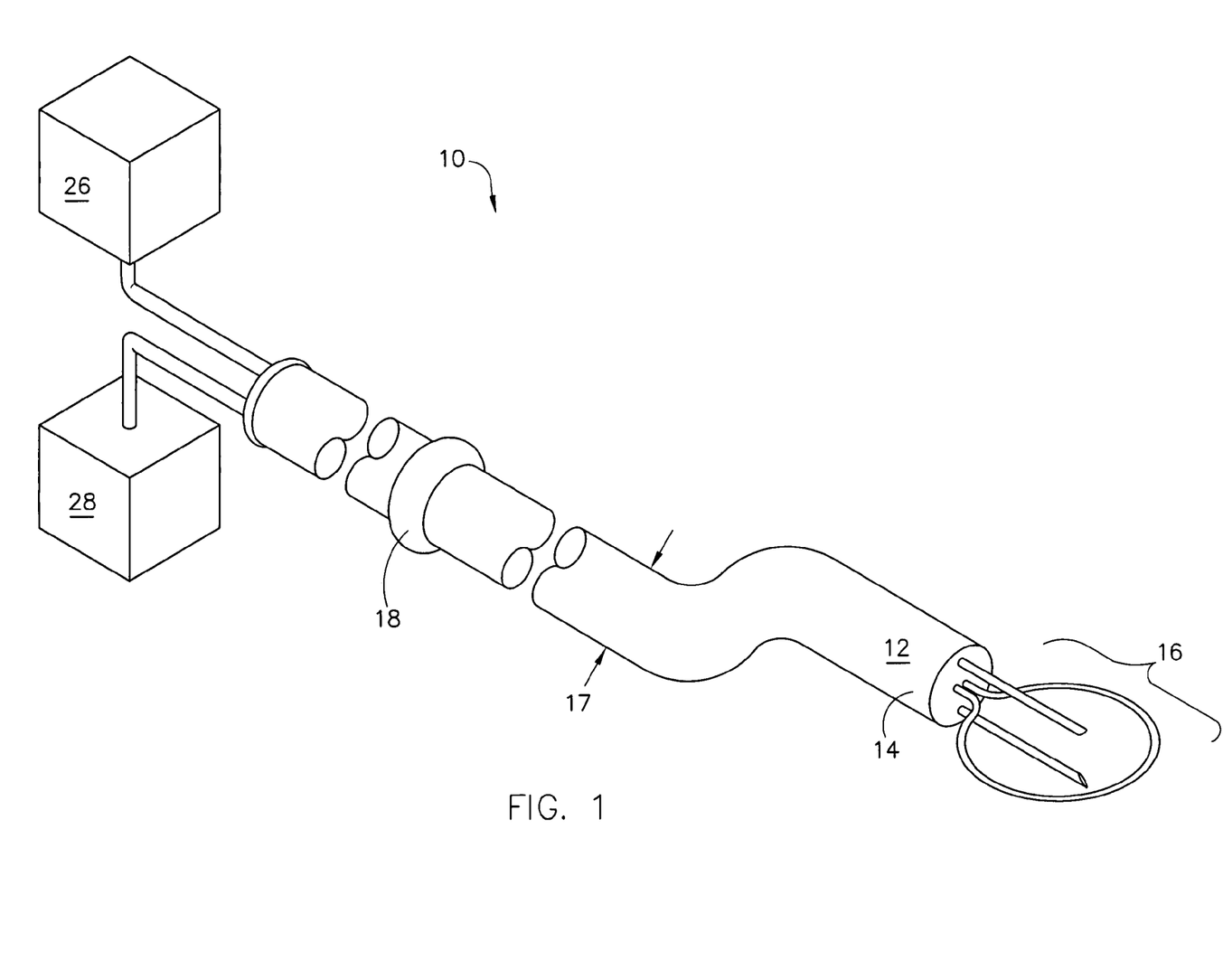
FIG. 1 is a perspective of a first embodiment of a medical device according to the present invention.

The needles 20 are communicative with an energy source 26, as shown in FIG. 1. The energy source 26 delivers energy to the needles 20 during the therapeutic procedure. Although other energy sources may be used without departing from the scope of the present invention, in one embodiment the energy source 26 is an electrical generator for delivering electrical current to the needles 20. Although such an electrical generator may produce electrical current having other characteristics without departing from the scope of the present invention, in one embodiment it produces a current having a voltage of between about 10 volts and about 500 volts and a frequency between about 0.3 megahertz and about 1.0 megahertz. In another embodiment, the energy source 26 is a radio frequency generator for delivering radio frequency energy to the needles 20. Although such a radio frequency generator may produce signals with other characteristics without departing from the scope of the present invention, in one embodiment the radio frequency generator produces a signal having an amplitude of between about 10 volts and about 500 volts and a frequency between about 0.3 megahertz and about 1.0 megahertz. In yet another embodiment, the energy source 26 delivers ultrasonic energy to the injection needles 20. Although such an ultrasonic generator may produce signals having other characteristics without departing from the scope of the present invention, in one embodiment the ultrasonic generator produces a signal having a frequency in the range of about 10 kilohertz to about 100 kilohertz.

In one embodiment of the present invention, at least two of the injection needles 20 can be of opposite polarity when the medical device 10 is in use. For example, with either the radio frequency or the electrical power generators 26, the needles 20 can be of opposite polarity. Such bipolar energy transmission is generally safer than mono-polar energy applications which can create coagulation zones that are too deep. Also, the characteristics of each needle 20, when such characteristics vary as described, may change. That is, the characteristics of each needle 20 may alternate or otherwise change with time during use of the medical instrument 10. Such varying signal characteristics, or multiplexing, results in higher levels of energy concentrated at and delivered from the needles 20 as a result of the interaction of differing signals between the adjacent needles.

The needles 20 also communicate with a fluid source 28 as shown in FIG. 1. The fluid source 28 delivers an electrically conductive fluid to the needles during the therapeutic procedure. Although other fluid sources may be used without departing from the scope of the present invention, in one embodiment the fluid source 28 is a conventional saline source for delivering saline to the needles 20.

Figure 5:
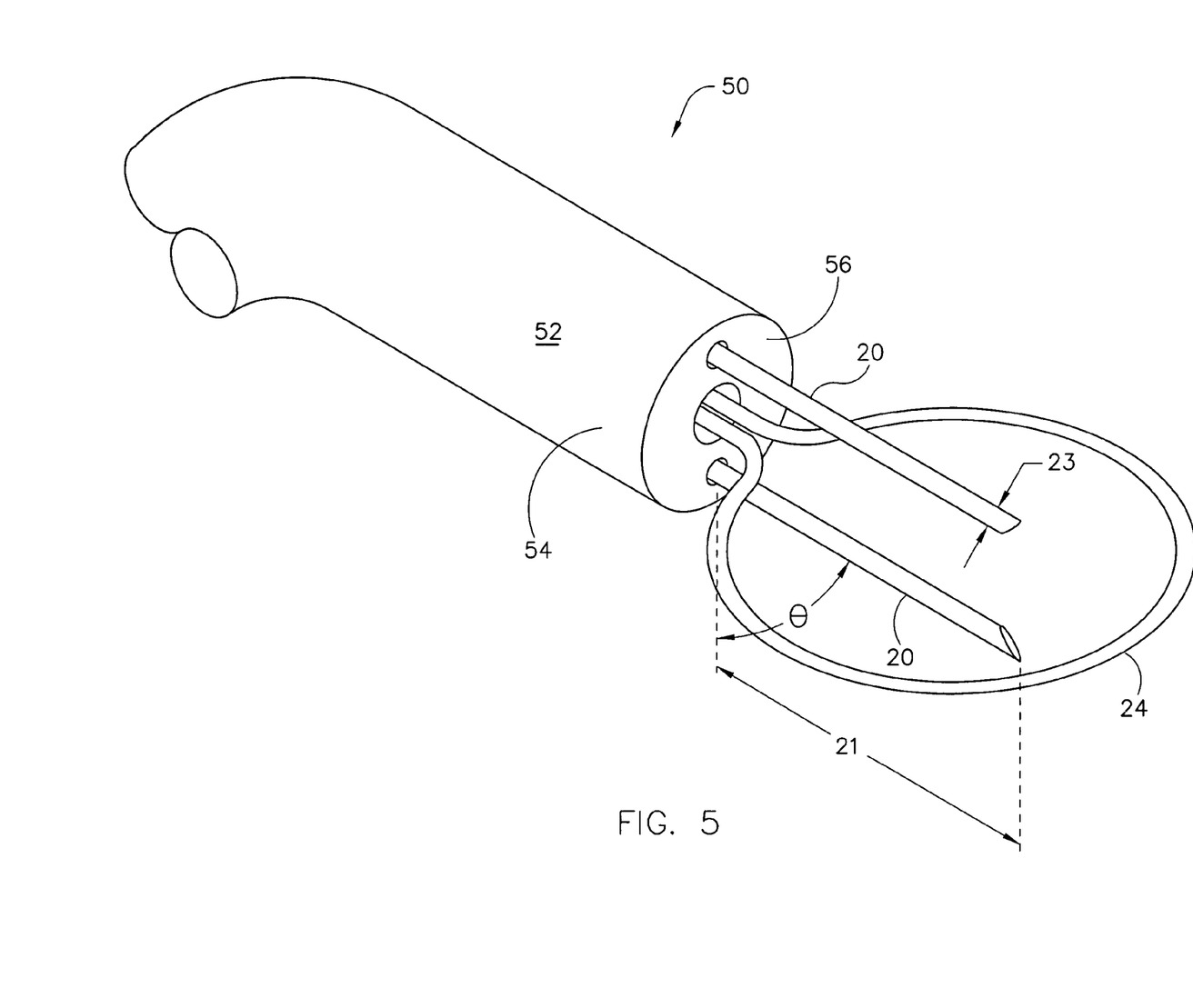
FIG. 5 is a detail perspective of a second embodiment of a medical device according to the present invention.
Figure 6:
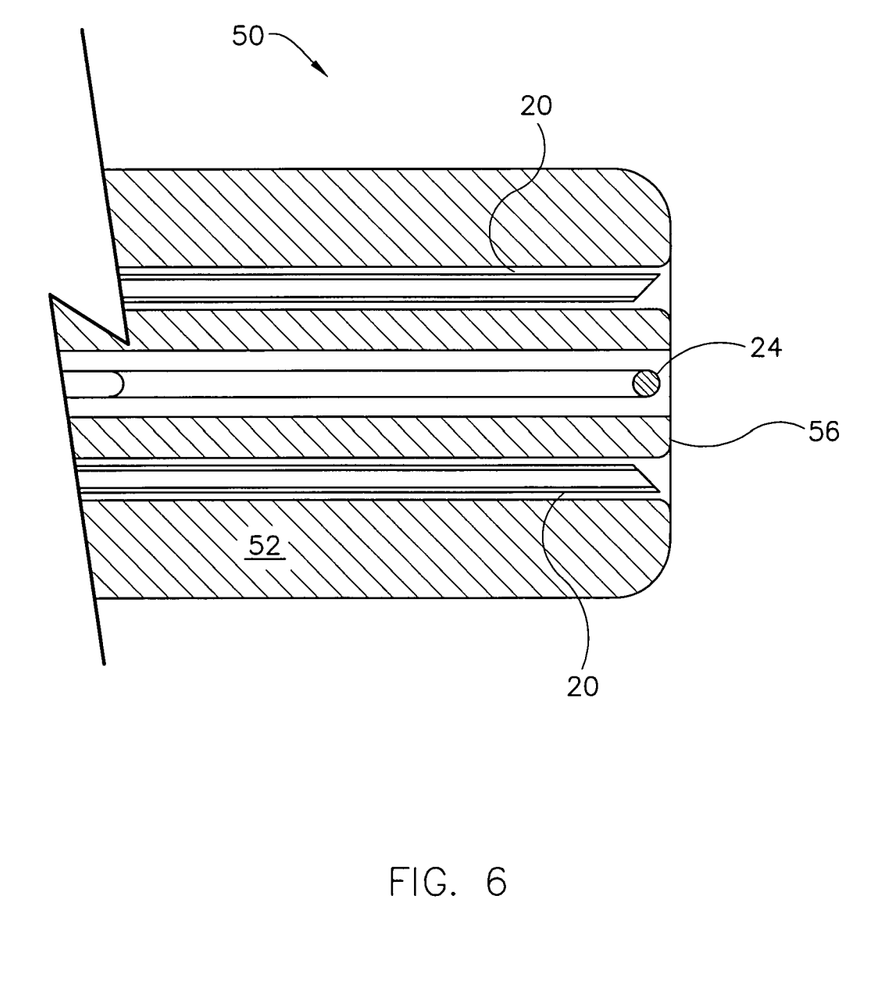
FIG. 6 is a detail side cross section of the embodiment of a medical device shown in FIG. 5 having stored needles and spreader.
Figure 7:
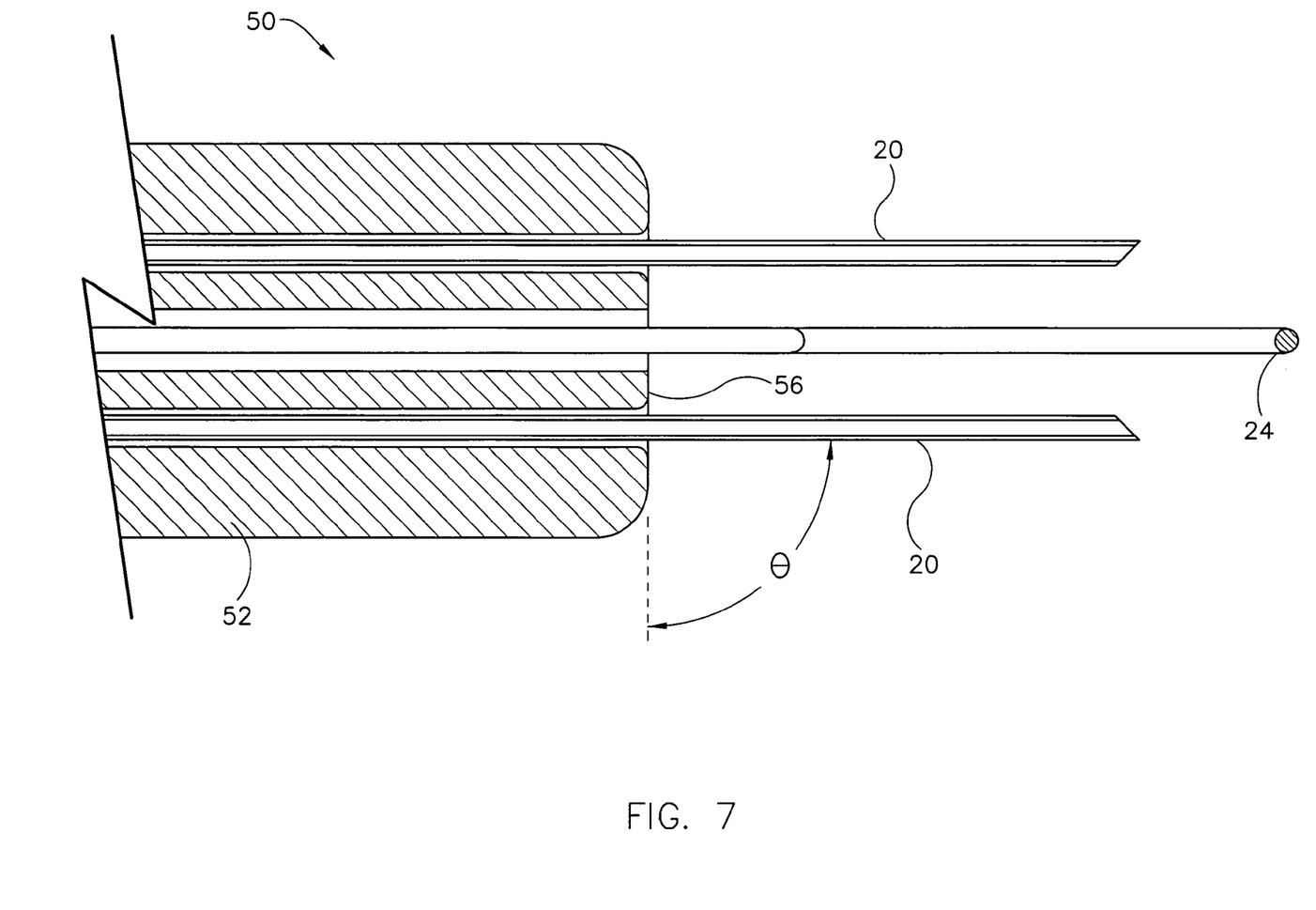
FIG. 7 is a detail side cross section of the embodiment of a medical device shown in FIG. 5 having deployed needles and spreader.

FIGS. 5-7 show a second embodiment of a medical device 50 according to the present invention in which the injection needles 20 and spreader 24 are slidably disposed within the elongate probe 52. In this embodiment, the needles 20 and spreader 24 can be moved between two or more positions. For example, FIG. 6 shows the needles 20 and spreader 24 in a stored position in which the needles and spreader are retracted into the probe 52. FIG. 7 shows the needles 20 and spreader 24 in a deployed position in which the needles and spreader extend beyond the applicator end 54 of the probe 52. The needles 20 extend out of the probe 52 at an angle θ with the face 56 of the applicator end 54 of the probe. Although FIG. 7 shows an angle θ of approximately 90 degrees, the needles 20 may extend from the probe face 56 at other angles without departing from the scope of the present invention. For example, the needles 20 may move out of the probe at an angle θ between about 45 degrees and about 90 degrees. The probe 52, needles 20, and spreader 24 of this embodiment are otherwise identical to the probes, needles, and spreaders of the first embodiment, and therefore will not be described in further detail.

Figure 8:
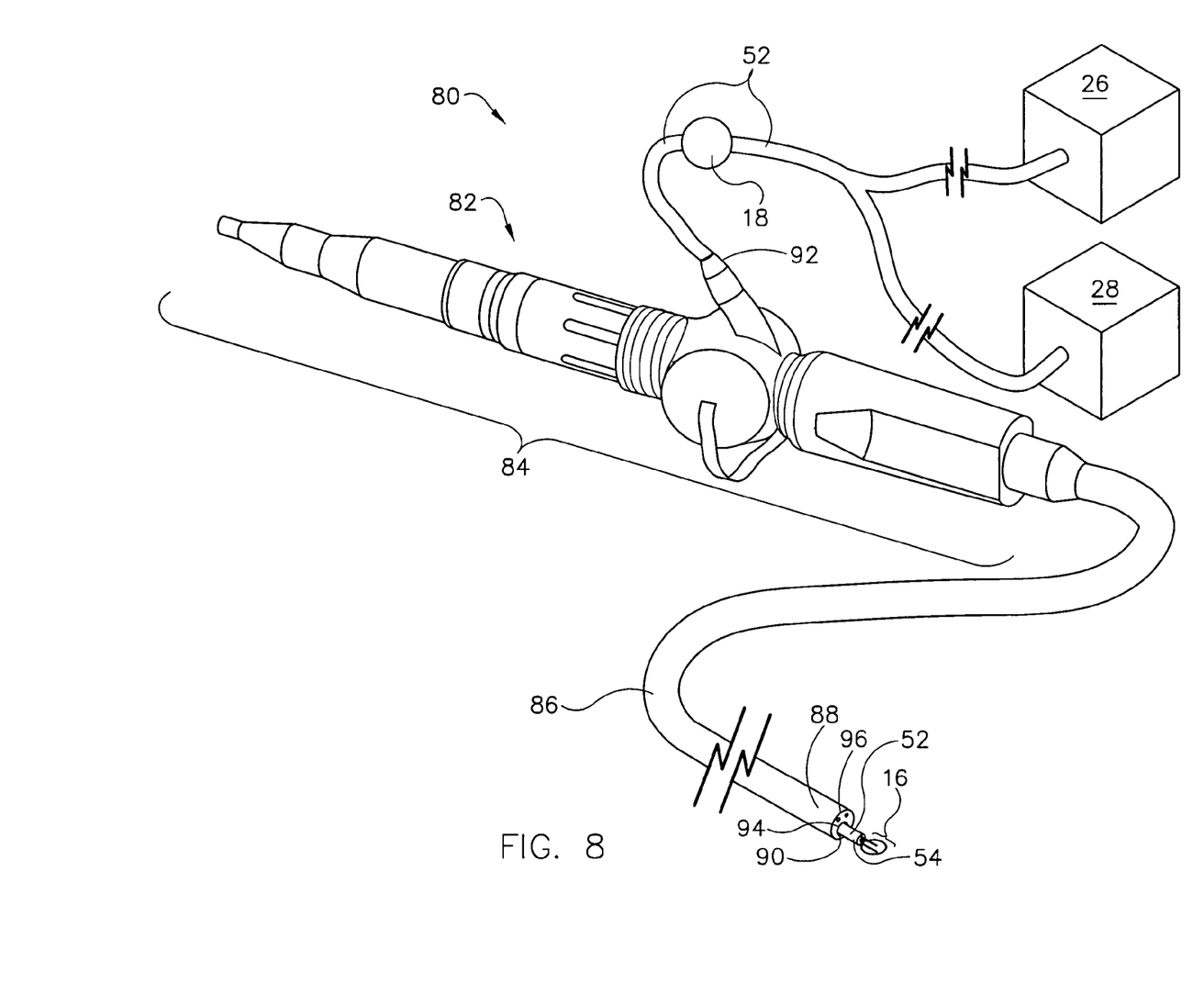
FIG. 8 is a perspective of the device in combination with a conventional endoscope.

FIG. 8 shows a third embodiment of a medical device 80 according to the present invention including an endoscope 82. Although FIG. 8 shows one type of endoscope 82, any conventional type of endoscope may be used without departing from the scope of the present invention. The endoscope 82 may be a flexible endoscope, such as those commonly used in upper gastrointestinal endoscopy examinations, or esophagogastroduodenoscopy (EGD). The endoscope 82 has an elongate primary body 84 and an elongate tubular portion 86 (e.g., a flexible shaft) extending from the body 84 to a working end 88. The endoscope 82 also has a working channel 90 beginning at an entry orifice 92 on the primary body 84 and terminating at a terminal port 94 at the extreme end 96 of the shaft 86. The working channel of conventional endoscopes has a diameter, or minimum width if non-circular, of about three millimeters. In one embodiment of the present invention, the probe 52, needles 20, and spreader 24 are sized and shaped for slidable receipt within the working channel 90 of the endoscope 82. The probe 52, needles 20, and spreader 24 of this embodiment are otherwise identical to the probes, needles, and spreaders of the earlier described embodiments, and therefore will not be described in further detail.

Figure 9:
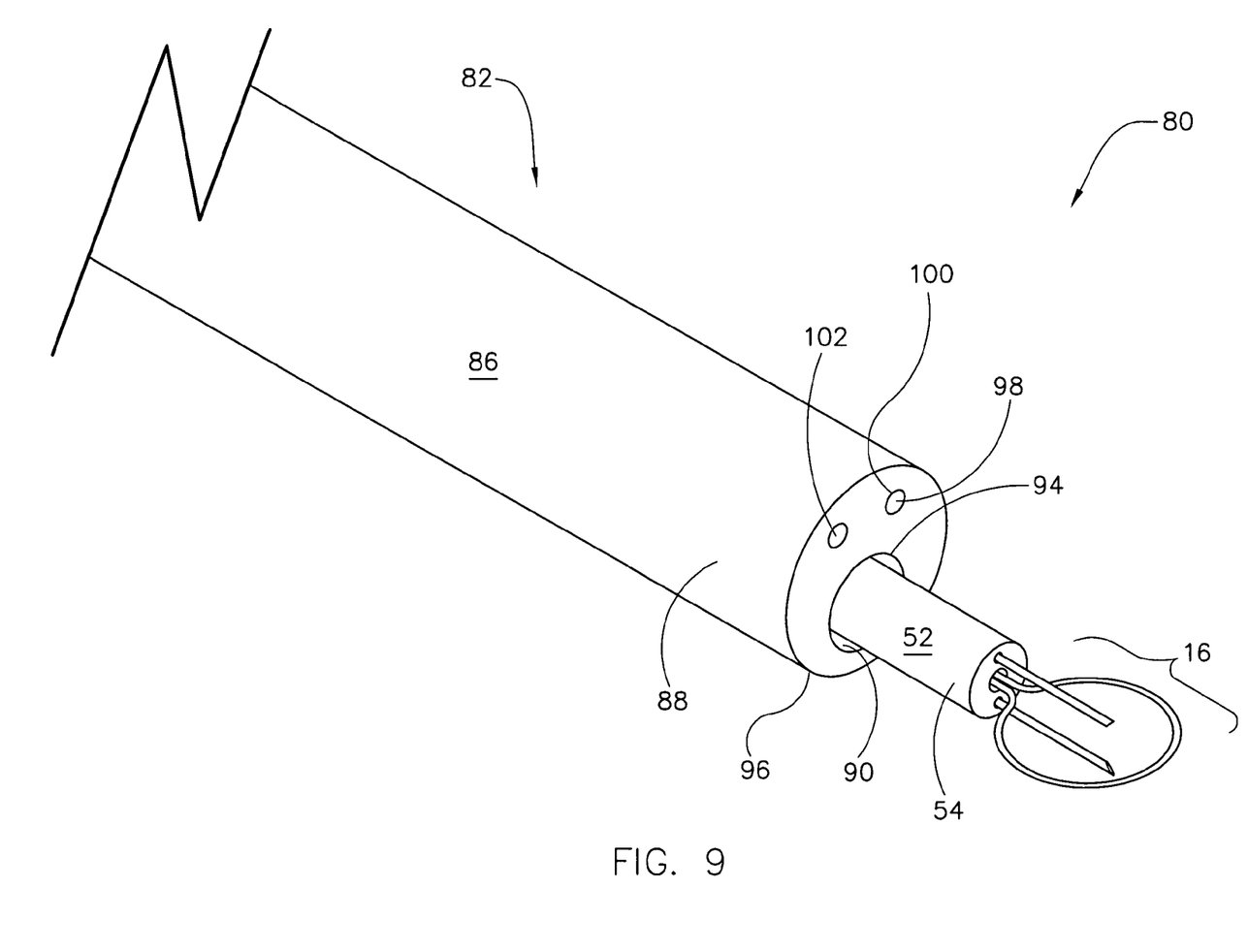
FIG. 9 is a detail perspective of a portion of the combination shown in FIG. 8.

As shown in FIG. 9, the medical device 80 can have viewing optics 98 for viewing an object (not shown) positioned in a viewing area (not shown) adjacent the working end 88 of the endoscope 82. The viewing area comprises all the objects visible through the viewing optics 98, including the applicator elements 16 and adjacent patient tissue (not shown in FIGS. 1-9). Although the viewing area may have other shapes without departing from the scope of the present invention, in one embodiment the area is circular. The optics 98 are disposed within the endoscope 82, beginning at a location (not shown) near the primary body 84, where a user may receive images, and terminating near an optics orifice 100. The endoscope 82 further has an illuminator 102 for directing light toward an object (not shown) positioned adjacent the working end 88 of the shaft 86. As with the optics 98, the illuminator 102 originates at a location (not shown) near the primary body 84 and terminates near the extreme end 96 of the shaft 86.

A primary purpose for the ablation device is to ablate diseased esophageal tissue for combating Barrett's esophagus. Although the medical device is described as ablating abnormal esophageal mucosa in humans, the device may ablate other tissues, tissues in other animals, or things other than tissue without departing from the scope of the present invention.

Figure 10:
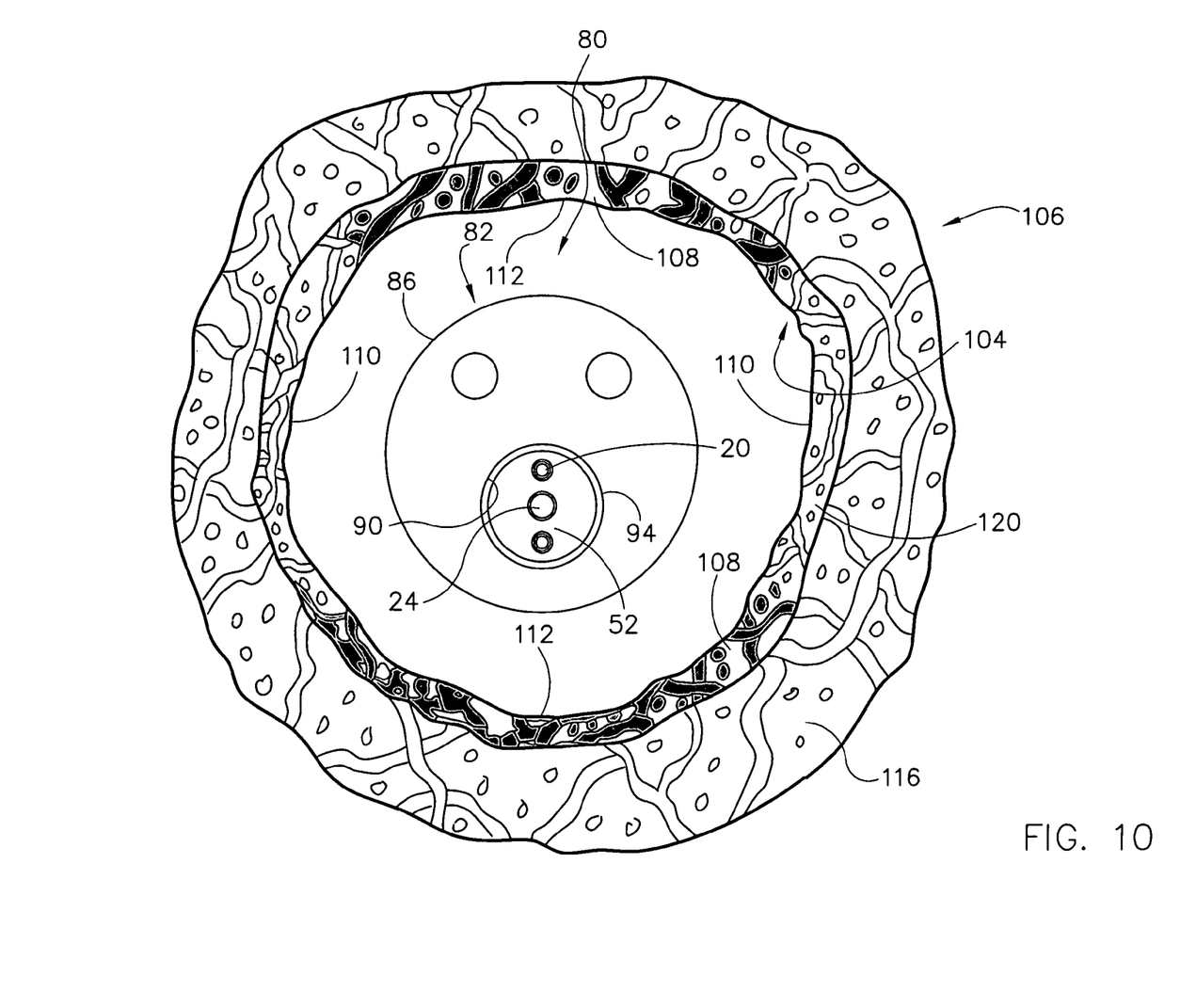
FIG. 10 is detail front cross section of the combination shown in FIG. 8 disposed in a patient with applicator elements stored in the probe.

In operation, a user of an ablation device 80 according to the present invention first positions the elongate probe 52 in the working channel 90 of the endoscope 82. The injection needles 20 are connected to an energy source 26 and a fluid source 28 as shown in FIGS. 1 and 8. FIG. 10 shows a probe 52 slidably disposed in an endoscope working channel 90 and the endoscope/probe combination disposed within a cavity or lumen 104 such as an esophagus of a patient 106. The user moves the endoscope 82 and probe 52 to a desired location within the patient 106. If desired, the user can verify that the probe 52 and endoscope 82 are properly positioned by viewing the patient 106 and applicator elements 16 positioned at the end 54 of the probe 52. The desired location is adjacent diseased lumenal tissue 108. Positioning the endoscope 82 and probe 52 may include articulating the shaft 86 of the endoscope 82, translating the endoscope 82, rotating the probe 52 with respect to the endoscope 82, and/or translating the probe 52 with respect to the endoscope 82.

Figure 11:
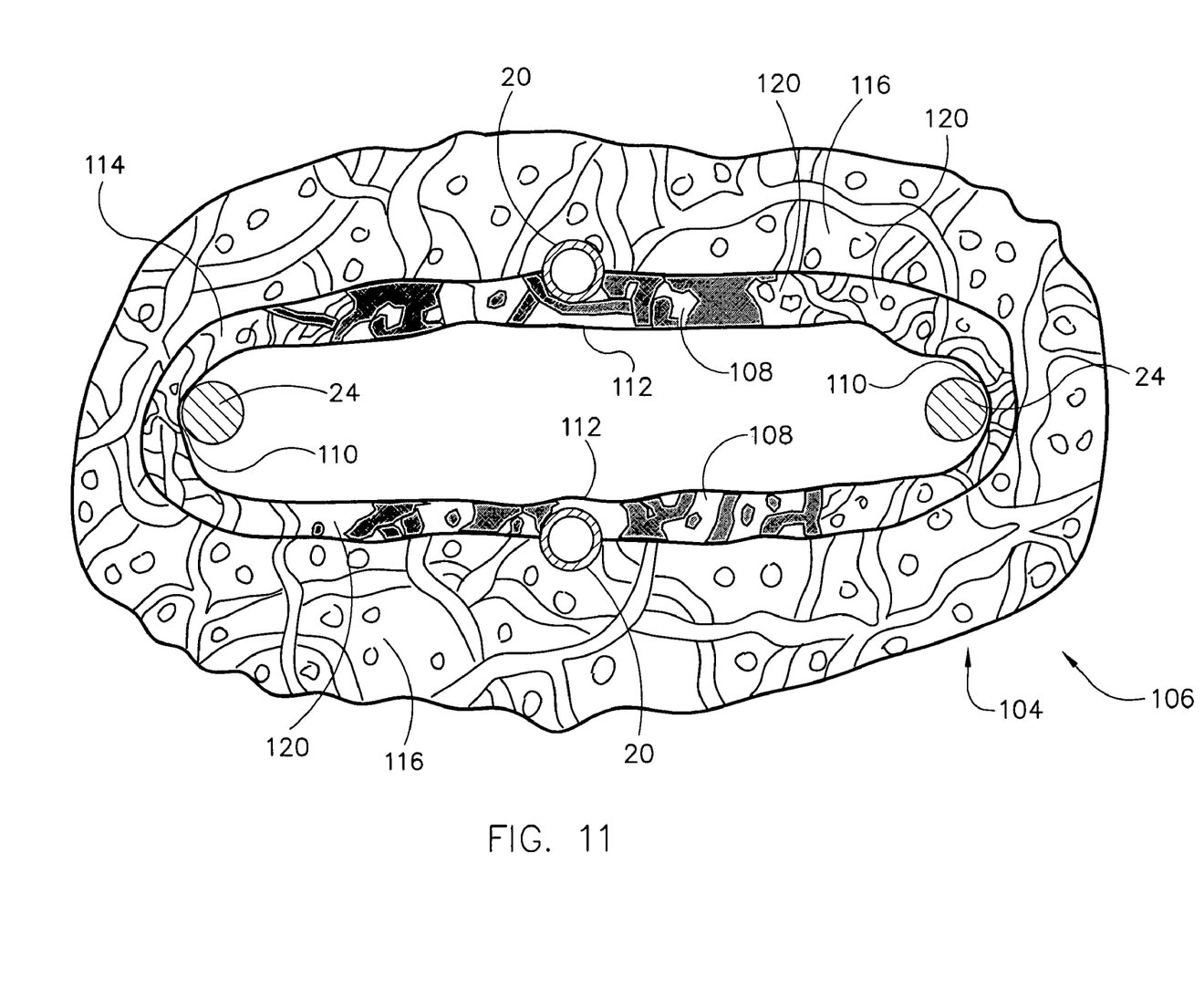
FIG. 11 is a detail front cross section of the combination shown in FIG. 8 in a patient having deployed applicator elements.
Figure 12:
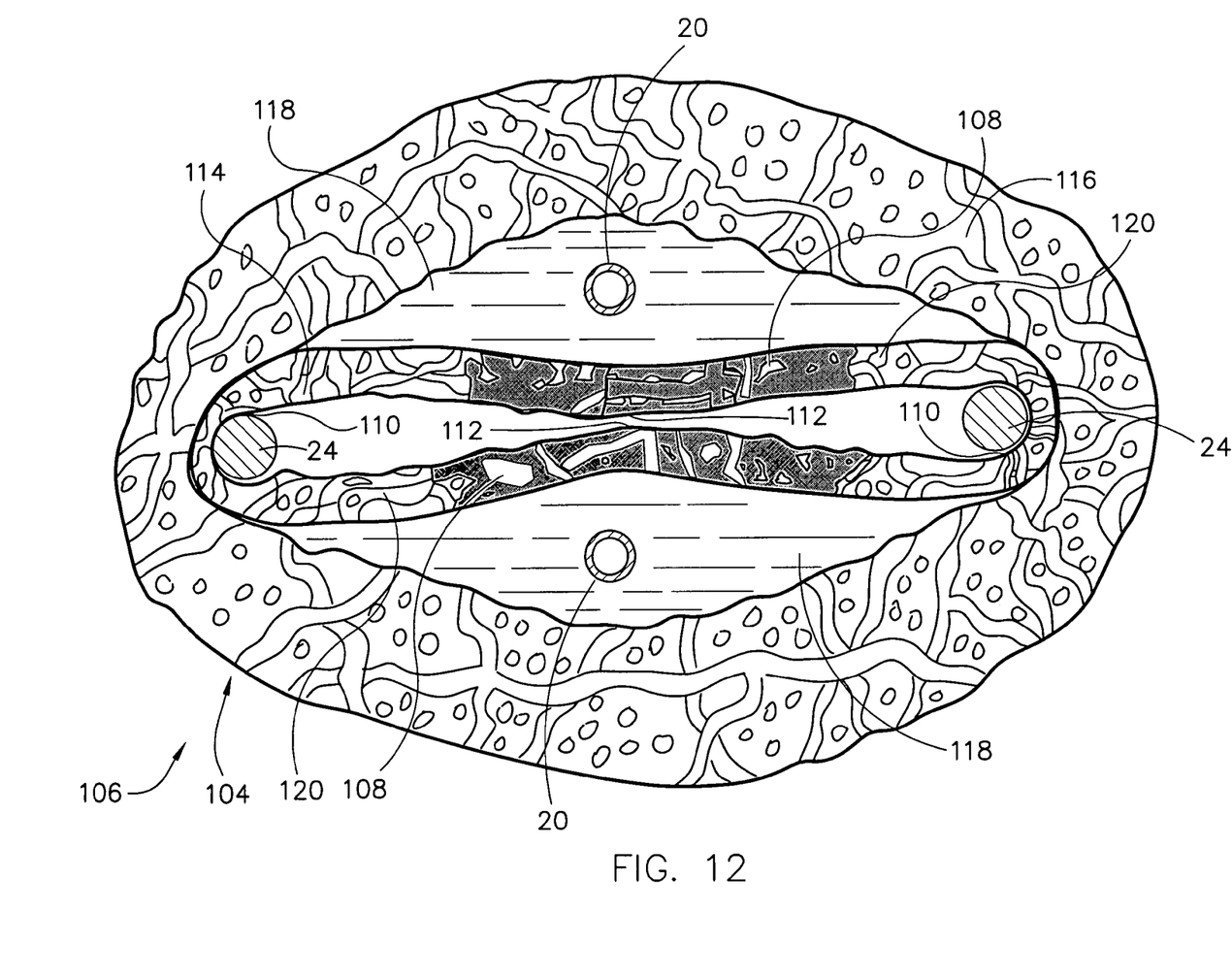
FIG. 12 is a detail front cross section of the combination shown in FIG. 8 in a patient after fluid has been injected through the needles into the patient.

Once the medical device 80 has been positioned as described, the user deploys the needles 20 and spreader 24 such that the needles and spreader extend through the port 94 of the working channel 90 at the working end 88 of the endoscope 82. As shown in FIG. 11, the spreader 24, when deployed, presses against opposite sides 110 of the lumen 104 in which the device is being used. This spreading causes points 112 on the lumen 104 between the opposite sides 110 to come closer together. As the needles 20 are deployed, they advance below the inner layer or surface 114 of the lumen 104 at points 112. In one embodiment, it is preferred that the needles 20 are forced to a position between the inner layer 114 and the muscular layer 116 underlying the inner layer 114. After the needles 20 are forced below the inner layer 114 of the lumen 104, fluid 118 is injected into the lumen 104 through the needles 20, thereby causing the points 112 on the lumen 104 between the opposite sides 110 to move closer together, as shown in FIG. 12. Then, the user can destroy the targeted tissue 108 of the patient 106 located between the needles 20 by energizing the needles 20. During the ablation, healthy adjacent tissue 120 is substantially unharmed because the energy transmission focuses between the needles 20, where the diseased tissue 108 is located but the healthy adjacent tissue is not. The healthy adjacent tissue 120 is also substantially unharmed during ablation because the spreading of the lumen 104 and the injection of fluid 118 cause the healthy adjacent tissue 120 to be spaced from the needles 20. The muscular tissue 116 underlying the target tissue 108 is also substantially unharmed during ablation of the target tissue 108 because the energy transmission focuses between the needles 20. The muscular tissue 116 is also substantially unharmed because the injection of fluid 118 into the lumen causes the muscular tissue 116 to be spaced from the needles 20.

By this local and accurate ablation method, diseased mucosal tissue 108 is destroyed and healthy adjacent mucosal tissue 120 and underlying muscular tissue 116 are substantially unharmed. A short period of time after the procedure, the destroyed tissue will be sloughed off through the normal digestive process and healthy mucosal tissue will grow in its place. The type of energizing may be of any conventional type, including the types mentioned above regarding energy source 26, such as radio frequency, electrical, and ultrasonic. Although the therapeutic method described was described with reference to medical device 80, it will be appreciated by those skilled in the art that the method can be performed in a substantially similar manner using any of the disclosed embodiments without departing from the scope of the present invention.

Although a preferred use of the medical device is to ablate tissue in a patient, the device may also be used on materials other than tissue. In view of the above, it will be seen that the several objects of the invention are achieved.

When introducing elements of the present invention or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A medical device for performing a therapeutic procedure on a patient comprising:
   a probe having an applicator end;
   at least two spaced and parallel injection needles connected to the probe adjacent said applicator end, each of said needles being communicative with a fluid source for delivering fluid to the respective needle and an energy source for delivering energy to the respective needle when performing the therapeutic procedure on the patient; and
   a spreader spaced from the needles and positioned adjacent the applicator end between the injection needles for spreading tissue of the patient during the therapeutic procedure, wherein the spreader includes a loop.

2. A medical device as set forth in claim 1 wherein the probe is an elongate probe sized and shaped to be slidably received in a working channel of said endoscope.

3. A medical device as set forth in claim 2 wherein the spreader and injection needles are slidably disposed within the elongate probe such that the spreader and the needles are movable between a stored position in which the spreader and needles are retracted into the probe to prevent contact between the needles and the patient and a deployed position in which the spreader and needles extend past the applicator end of the probe to allow contact between the needles and the patient.

4. A medical device as set forth in claim 2 wherein the probe has a maximum width of less than about three millimeters.

5. A medical device as set forth in claim 2 wherein the fluid source comprises a saline source for delivering saline to the injection needles.

6. A medical device as set forth in claim 2 wherein the energy source comprises an electrical source for selectively delivering electrical energy to the injection needles.

7. A medical device as set forth in claim 6 wherein the electrical source comprises an ultrasonic source for selectively delivering ultrasonic energy to the injection needles.

8. A medical device as set forth in claim 6 wherein the electrical source comprises a radio frequency source for selectively delivering radio frequency energy to the injection needles.

9. A medical device as set forth in claim 8 wherein, during operation of the device, the injection needles are oppositely charged.

10. A medical device as set forth in claim 9 wherein, during operation of the device, the charge on each injection needle changes with time.

11. A medical device as set forth in claim 1 wherein the loop is resilient.

12. A medical device as set forth in claim 1 wherein the loop is moveable between a retracted position in which laterally opposite sides of the spreader are adjacent each other and an extended position in which the sides are spaced from each other.

13. A medical device for performing a therapeutic procedure on a patient comprising:
    an elongate endoscope extending to a working end and having optics for viewing an object positioned in a viewing area adjacent said working end;
    a probe having an applicator end positioned adjacent the working end of the endoscope;
    at least two spaced and parallel injection needles positioned adjacent the applicator end of the probe in the viewing area, each of said injection needles being communicative with a fluid source for delivering fluid to the respective needle and an energy source for delivering energy to the respective needle when performing the therapeutic procedure on the patient; and
    a spreader spaced from the needles and positioned adjacent the applicator end of the probe between the injection needles for spreading tissue of the patient during the therapeutic procedure;
    wherein the endoscope has a working channel extending along the endoscope and the probe is slidably disposed in said working channel.

14. A medical device as set forth in claim 13 wherein the spreader and injection needles are slidably disposed within the probe such that the spreader and the needles are movable between a stored position in which the spreader and needles are retracted into the probe and a deployed position in which the spreader and needles extend past the applicator end of the probe.

15. A medical device for performing a therapeutic procedure on a patient comprising:
- an elongate endoscope extending to a working end and having optics for viewing an object positioned in a viewing area adjacent said working end;
- a probe having an applicator end positioned adjacent the working end of the endoscope;
- at least two spaced and parallel injection needles positioned adjacent the applicator end of the probe in the viewing area, each of said injection needles being communicative with a fluid source for delivering fluid to the respective needle and an energy source for delivering energy to the respective needle when performing the therapeutic procedure on the patient; and
- a spreader spaced from the needles and positioned adjacent the applicator end of the probe between the injection needles for spreading tissue of the patient during the therapeutic procedure, wherein the spreader is moveable between a retracted position in which laterally opposite sides of the spreader are adjacent each other and an extended position in which the sides are spaced from each other.

* * * * *